United States Patent [19]
Ferrier

[11] Patent Number: 6,046,843
[45] Date of Patent: Apr. 4, 2000

[54] LIGHT COLLECTOR FOR HIGH MAGNIFICATION INSPECTION

[75] Inventor: Mark S. Ferrier, Corvallis, Oreg.

[73] Assignee: Hewlett-Packard Company, Palo Alto, Calif.

[21] Appl. No.: 09/173,569

[22] Filed: Oct. 15, 1998

[51] Int. Cl.$^7$ .............................. G02B 9/06; G02B 21/36; G02B 21/00
[52] U.S. Cl. .......................... 359/362; 359/363; 359/364; 359/381; 356/237.1; 351/219
[58] Field of Search ..................... 359/362, 363, 359/380, 381, 368, 391; 351/219; 356/237.1; 600/166

[56] References Cited

U.S. PATENT DOCUMENTS

| | | | |
|---|---|---|---|
| 4,655,555 | 4/1987 | Machler et al. | 350/432 |
| 4,680,635 | 7/1987 | Khurana | 258/211 |
| 4,720,191 | 1/1988 | Siegel et al. | 250/563 |
| 4,900,932 | 2/1990 | Schafer et al. | 250/397 |
| 4,929,041 | 5/1990 | Vahala et al. | 350/96.1 |
| 5,264,704 | 11/1993 | Phang et al. | 250/347 |
| 5,588,949 | 12/1996 | Taylor et al. | 600/166 |
| 5,724,131 | 3/1998 | Chim et al. | 356/327 |

OTHER PUBLICATIONS

Yakubenas et al, Sov. J. Opt. Tech., 38, No. 1, Jan. 1971.

*Primary Examiner*—Cassandra Spyrou
*Assistant Examiner*—Fayez Assaf

[57] ABSTRACT

An optical element for microscopic inspection of a surface. The optical element has an elongated body defining an optical axis, with a first end adjacent the surface and a second end directed toward an imaging instrument. The body has a curved reflective surface and an optical aperture at the first end, and defines first and second associated focal points on the optical axis. The first focal point is spaced apart from the first end of the body, such that positioning the surface at the first focal point generates an image of the surface at the second focal point. The reflective surface may be paraboloidal, with a concentrating lens focusing collimated rays to the second focal point, so that a conventional microscope may view the image generated at the second point.

20 Claims, 3 Drawing Sheets

LIGHT COLLECTOR FOR HIGH MAGNIFICATION INSPECTION

FIELD OF THE INVENTION

This invention relates to microscopy, and more particularly to efficient collection of low-light images.

BACKGROUND AND SUMMARY OF THE INVENTION

Semiconductor chips may be analyzed for certain defects by detecting small amounts of light emitted by such defects. Typically, inspection is conducted either by low magnification lenses having relatively large numerical aperture to enhance light gathering capacity, or by higher powered microscopes operating at close spacing to the surface being analyzed. A chip may be scanned or imaged, and the result analyzed to determine defect characteristics and locations to enable design improvements and process quality control. While effective in some circumstances, these inspection methods and apparatus have significant limitations.

Both of the above detection techniques suffer from inherent limitations in light gathering capacity. Even a costly large aperture lens captures only a limited "cone" of light rays from an emission point, typically a small minority of light flux emitted. Further, in many circumstances, the light source is neither equally bright at all viewing angles nor emitted in a lambertian pattern. Often, light is emitted more laterally than axially. For instance, when there is significant metallization immediately above a light-emitting defect, there may be little or no detectable light emitted vertically (from the horizontal surface) or within the limited offset angle collected by conventional lenses; most or all emissions may be predominately lateral.

High powered microscope objectives may have a moderately high acceptance angle, which is the angle subtended by the lens from the point being imaged. For emissions having a significant vertical distribution, these objectives may have acceptable light gathering capacity, because the optical axis is aligned vertically with the sample. Often, only a minority of rays are captured, limiting detection of sources at a low brightness threshold, or requiring larger dwell times during scanning to collect adequate light flux to activate sensors. Even where such optics perform adequately, they are unacceptable for inspecting large portions of packaged semiconductor chips near bond wires. Such bond wires protrude upwardly at the periphery of most chips, and are necessary to provide electrical connection between the chip and the external circuitry which stimulates light emissions from defects. High powered microscope lenses must be positioned closer to the surface being inspected than the typical height of bond wires. Thus, the significant diameter of such lenses prohibits their use for inspection of chip regions closer to wire bonds than one radius of the lens housing. Because such lens housing diameters may be comparable in size to chip dimensions, only a small central portion of many chips may be inspected by such microscopes.

The present invention overcomes the limitations of the prior art by providing an optical element for microscopic inspection of a surface. The optical element has an elongated body defining an optical axis, with a first end adjacent the surface and a second end directed toward an imaging instrument. The body has a curved reflective surface and an optical aperture at the first end, and defines first and second associated focal points on the optical axis. The first focal point is spaced apart from the first end of the body, such that positioning the surface at the first focal point generates an image of the surface at the second focal point. The reflective surface may be paraboloidal, with a concentrating lens focusing collimated rays to the second focal point, so that a conventional microscope may view the image generated at the second point.

DETAILED DESCRIPTION OF A PREFERRED EMBODIMENT

Figure 1:
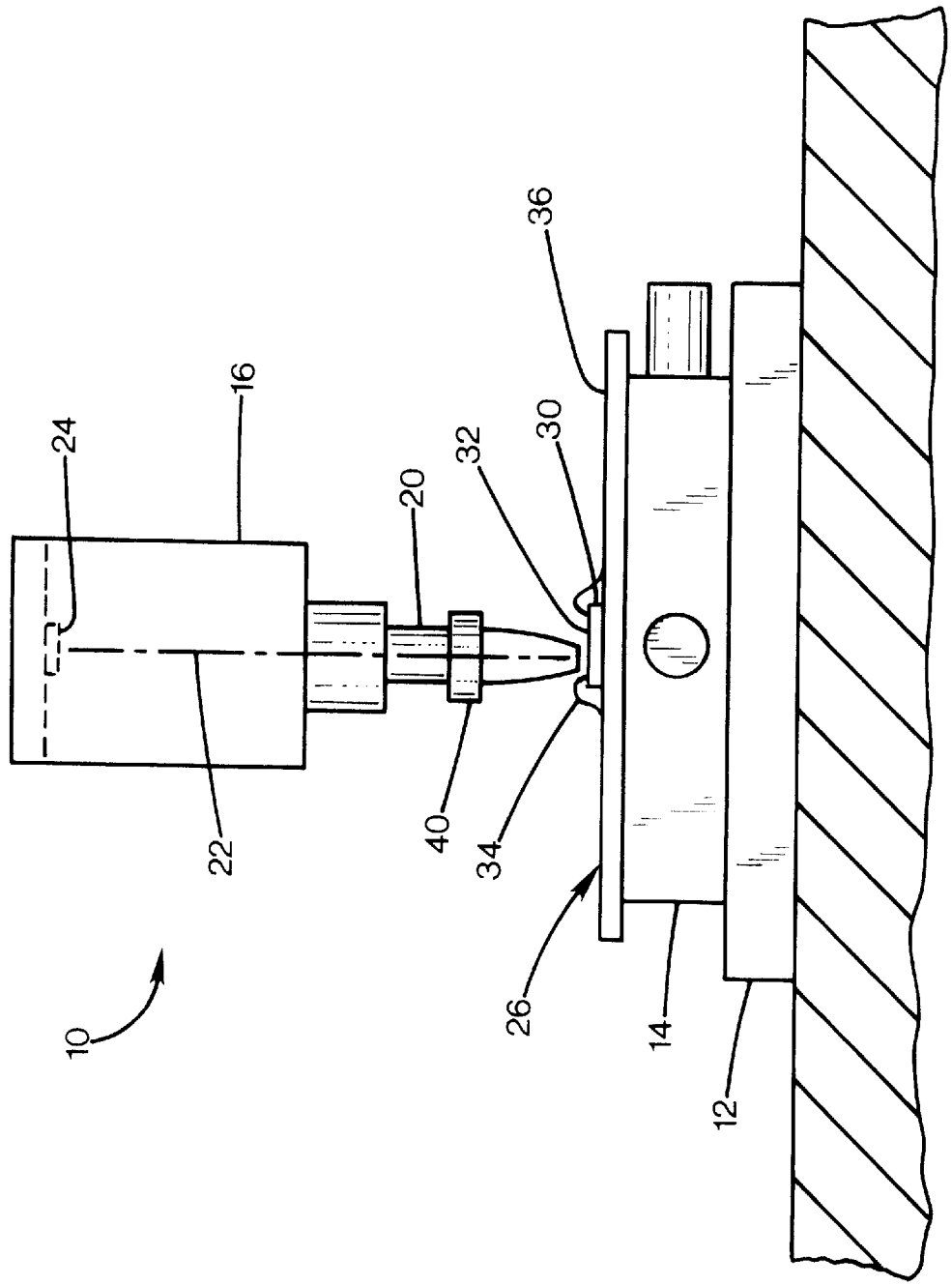
FIG. 1 is a simplified elevational view of an optical microscope including a light collector element according to a preferred embodiment of the invention.

FIG. 1 shows a microscope 10 having a base 12 supporting a movable stage 14, with an imaging portion 16 having an optical objective lens assembly 20 on an optical axis 22. An imager such as a photodetector 24 is positioned within the imaging portion on the optical axis. A semiconductor device 26 is positioned on the stage, and includes a chip 30 having an upwardly-facing surface 32 normal to the optical axis. A plurality of bond wires 34 extend upward and laterally from peripheral locations on the upper surface of the chip, and connect to a substrate 36 supporting the chip. The device is electrically connected to external circuitry to activate the chip so that certain defects may be revealed by light emissions from the defect locations.

Figure 2:
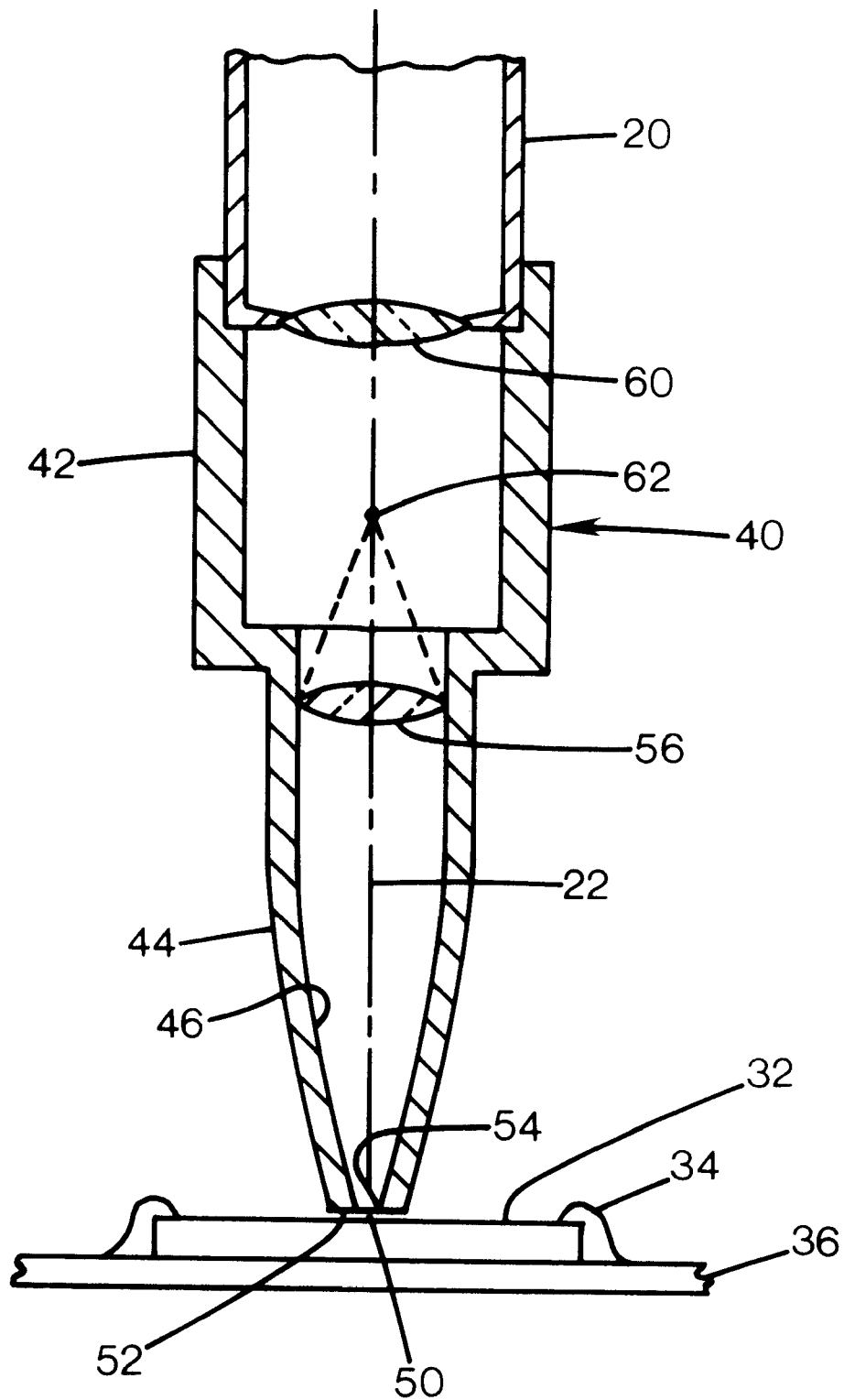
FIG. 2 is an enlarged sectional side view of the light collector of FIG. 1.

An optical reflector element 40 is connected to the objective lens 20, as shown in detail in FIG. 2. The reflector element is an elongated cylindrical body formed as a surface of revolution about the optical axis 22, with which it is coaxial. The element has a connection portion 42 that mechanically connects to the microscope objective lens housing, and which supports a downwardly extending reflector portion 44. The reflector portion defines a paraboloidal bore 46 having a specular surface that is aluminized for maximum reflectivity. The figure of the bore is defined to have a focal point 50 beyond a lower end 52 of the element. The lower end defines an aperture 54 defined by the intersection between the lower end surface and the paraboloidal figure.

The reflector element includes a concentrating lens 56 within or above the bore at the upper end of the reflective portion, entirely spanning the bore. The lens has a focal length less than the spacing between it and the front surface of the microscope objective lens 60. Thus a focal point 62 is formed where parallel rays from the reflector converge, such that the microscope may focus on the image formed at the focal point, at a typical working distance between 0.3 and 10 mm.

Figure 3:
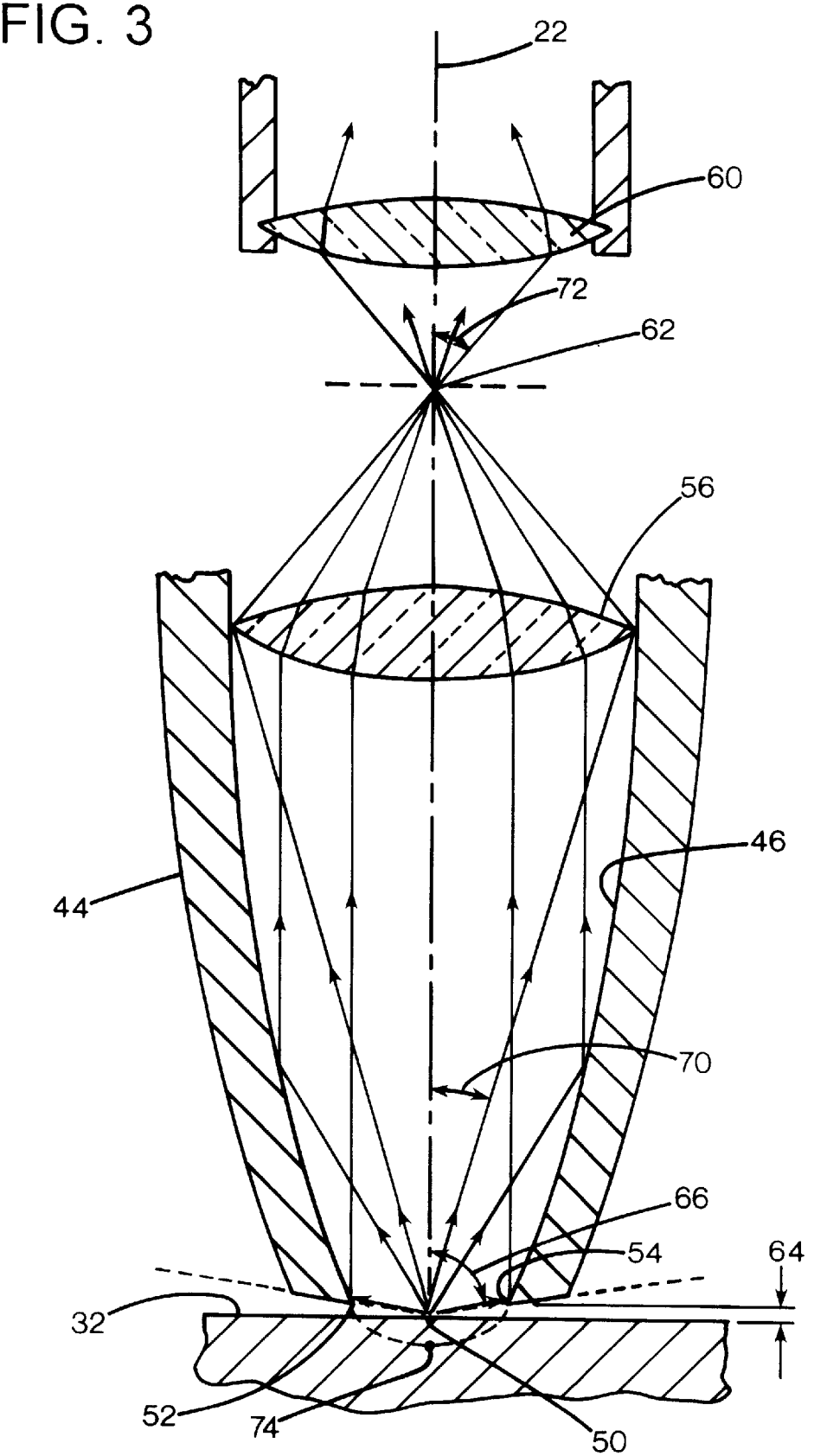
FIG. 3 is an enlarged sectional side view of the embodiment of FIG. 1 showing light ray paths.

FIG. 3 shows the reflector element in greater detail. With the parabolic focus point 50 at the surface, rays emitted from the point are largely captured by the reflector and collimated into a parallel bundle collected by lens 56 and focused to point 62. The lower free end 52 of the reflector is spaced apart from the focal point 50 by a gap 64 that is small relative to the diameter of the aperture 54. Preferably, a spacing of 5.0 μm is provided, with an aperture diameter of 110 μm. This provides an acceptance angle 66 of 84.8° off axis, so that substantially all light emitted by the surface point is collected, including a substantial portion of light emitted well off axis. In alternative embodiments, the spacing may be increased by limited amounts, but collection efficiency is sacrificed excessively when the ratio of aperture diameter to spacing drops below 2.

The on axis and slightly off axis rays that impinge directly on the concentrating lens 56 without first being collimated by the reflector are focused well beyond the focal point 62 of the lens 56, and thus are not usefully collected by the device. The efficiency-reducing effect of this loss is minimized by providing such an elongated reflector portion relative to the lens diameter that the half angle subtended by the lens is small. In the preferred embodiment, the length of the reflector is 15.0 mm, the lens diameter is 2.44 mm, providing a half angle 70 of 4.6°. Accordingly, the collection efficiency of the reflector (discounting any light losses along the optical paths) is 90.6%, based on the light lost at nearly lateral angles, and in the narrow on-axis cone of rays.

The rays output by the concentrating lens are contained within a bundle having a limited angle defined by the lens diameter and focal length. In the preferred embodiment, with the parameters disclosed above, useful rays focused by the reflector and lens are contained in a bundle having a half angle 72 of about 11°. By narrowing the light flux to such a narrow angle, the initially widely-dispersed rays are entirely usable by a readily available microscope objective having an acceptance angle greater than that amount.

The reflector and lens assembly thus provides several advantageous functions. First, it collects a large percentage of all emitted rays from a given point, particularly those rays emitted well off axis in a more lateral direction. Second, it emits those rays in a relatively narrow bundle so that all rays may be collected by a conventional microscope objective. Third, it forms an image of the surface point well above the surface, and has a narrow elongated shape that allows its positioning near wire bonds protruding above the surface. Although the lower end of the reflector tube is closer to the surface than the height of a wire bond, the tube has a limited radius of less than 1 mm at wire bond heights, so that the device may be used to inspect points as close as 1 mm from bond locations, or less. In contrast, typical large aperture microscope objectives have radial dimensions of about 10–12 mm or more, rendering them unsuitable for inspection near wire bonds.

In the preferred embodiment, the reflector assembly is used in conjunction with a conventional microscope. An objective lens with a working distance of 6.8 mm provides a lo magnifies the image formed at point 62 by a factor of 50 diameters. In the illustrated embodiment, to provide an elongated reflector shape, the paraboloid has a very short focal length of about 25 $\mu$m, which is the distance between point 50 and the vertex 74 of the curve, or about one fourth of the width of the curve at the plane of the surface 32 containing the focal point.

Although the system is believed to form an image at the focal point 62, and thereby form an image of the surface at the image plane of the microscope detector, the disclosed system is intended to function as a non-imaging point detector. The functional benefits are achieved by determining if any light is being emitted from the small region near the surface point 50. A scanning process is employed to search for and locate light emitting locations on the chip. The mere existence of such a site, together with its location, is typically adequate for analytical purposes.

The above system operates by installing a reflector assembly on a microscope objective so that the output focal point coincides with the microscope's point of focus. The device under test is positioned on the microscope stage, and is electrically connected and activated to stimulate light emission from defect sites. In a darkened environment, the chip is scanned by increments corresponding to the effective field of view of the detector system, with adequate dwell time at each position on the matrix of possible locations to collect adequate light to trigger the detector. After scanning, the location of any emission sites is recorded by the stage controller to facilitate failure analysis.

While the above is discussed in terms of preferred and alternative embodiments, the invention is not intended to be so limited. For instance, the reflector assembly may take any of a multitude of versions that form an image of the chip surface well above the surface. The reflector need not be parabolic, but may be any curved profile, such as an ellipsoid, that generates an image in conjunction with the concentrating lens. In other embodiments, the concentrating lens may be omitted, and an elliptical shape that tapers at the upper end as well as the lower may provide a focused image of the surface being analyzed.

What is claimed is:

1. An optical element for microscopic inspection of a surface, the optical element comprising:

an elongated body defining an optical axis, the body having a first end adjacent the surface and a second end directed toward an imaging instrument;

the body defining a curved reflective surface defining an optical aperture at the first end;

the optical element defining first and second associated focal points on the optical axis; and the first focal point being spaced apart from the first end of the body, such that positioning the surface at the first focal point generates an image of the surface at the second focal point.

2. The element of claim 1 wherein the reflective surface is a surface of revolution about the optical axis.

3. The element of claim 1 wherein the reflective surface is a paraboloid.

4. The element of claim 1 wherein the optical aperture has a radius greater than a distance by which the first focal point is spaced apart from the first end.

5. The element of claim 1 including a concentrating lens adjacent the reflective surface, such that the lens focuses parallel rays generated by the reflective surface to the second focal point.

6. The element of claim 1 wherein the body is a tube having a reflective interior surface.

7. The element of claim 1 wherein the optical aperture subtends a first angle with respect to the first focal point, and wherein the element has a second optical aperture at the second end, the second optical aperture subtending a second angle with respect to the second focal point less than the first angle.

8. The element of claim 1 including connection means for connecting the second end of the element to an objective lens of a microscope.

9. An optical inspection system comprising:

a microscope having a stage supporting a test element having a flat surface;

the microscope having an optical objective defining an optical axis perpendicular to the surface;

an elongated body connected to the optical objective in alignment with the optical axis;

the body having a first end extending away from the microscope and a second end connected to the optical objective;

the body defining a curved reflective surface defining an optical aperture at the first end;

the body defining first and second associated focal points on the optical axis; and the first focal point being positioned beyond the first end of the body, and the second focal point being positioned adjacent the microscope optical objective.

10. The system of claim 9 wherein the reflective surface is a surface of revolution about the optical axis.

11. The system of claim 9 wherein the reflective surface is a paraboloid.

12. The system of claim 9 wherein the optical aperture has a radius greater than a distance by which the first focal point is spaced apart from the first end.

13. The system of claim 9 including a concentrating lens between the reflective surface and the microscope objective, such that the lens focuses parallel rays generated by the reflective surface to the second focal point.

14. The system of claim 9 wherein the body includes a tube having a reflective interior surface.

15. The system of claim 9 wherein the optical aperture subtends a first angle with respect to the first focal point, and wherein the body has a second optical aperture at the second end, the second optical aperture subtending a second angle with respect to the second focal point less than the first angle.

16. A method of microscopically inspecting a surface comprising:

positioning the surface on a stage of a microscope having an objective lens defining an optical axis;

positioning the surface with a limited portion to be inspected on the optical axis;

forming an image of the limited portion at a focal point spaced apart from the surface and between the surface and the objective; and focusing the objective on the image.

17. The method of claim 16 wherein forming the image includes positioning an elongated reflective conduit above the limited portion.

18. The method of claim 16 wherein forming the image includes capturing rays emitted from the limited portion over a first range of angles offset from the optical axis, and transmitting the rays to the objective within narrower second range of angles, such that laterally emitted light is received by an objective having a relatively narrow angle of acceptance.

19. The method of claim 18 wherein the first range of angles includes rays emitted at angles offset from the optical axis by greater than 45 degrees.

20. The method of claim 16 wherein forming the image includes collimating rays emitted from the limited portion, and focusing the collimated rays to the focal point.

* * * * *